(12) United States Patent
Schelberger et al.

(10) Patent No.: US 6,541,500 B1
(45) Date of Patent: Apr. 1, 2003

(54) FUNGICIDE MIXTURE

(75) Inventors: Klaus Schelberger, Gönnheim (DE); Maria Scherer, Landau (DE); Reinhold Saur, Böhl-Iggelheim (DE); Josef Appel, Mutterstadt (DE); Joachim Leyendecker, Ladenburg (DE); Eberhard Ammermann, Heppenheim (DE); Thomas Grote, Schifferstadt (DE); Gisela Lorenz, Neustadt (DE); Siegfried Strathmann, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/868,724

(22) PCT Filed: Dec. 11, 1999

(86) PCT No.: PCT/EP99/09812

§ 371 (c)(1),
(2), (4) Date: Jun. 21, 2001

(87) PCT Pub. No.: WO00/36921

PCT Pub. Date: Jun. 29, 2000

(30) Foreign Application Priority Data

Dec. 22, 1998 (DE) .......................... 198 59 250

(51) Int. Cl.⁷ .................. A01N 43/64; A01N 43/40; A01N 43/56; A01N 43/84
(52) U.S. Cl. .............. 514/383; 514/312; 514/407; 514/236.2; 514/239.5; 514/317
(58) Field of Search ................. 514/312, 383, 514/407, 239.5, 317, 236.2

(56) References Cited

U.S. PATENT DOCUMENTS 5,240,940 A * 8/1993 Arnold et al. ............... 514/312

FOREIGN PATENT DOCUMENTS

| CA | 2195577 | 2/1996 |
|---|---|---|
| CA | 2208141 | 6/1996 |
| WO | 96/03047 | 2/1996 |
| WO | 96/18299 | 6/1996 |
| WO | 97/40673 | 11/1997 |
| WO | 97/40688 | 11/1997 |
| WO | 98/41094 | 9/1998 |
| WO | 98/54969 | 12/1998 |

* cited by examiner

Primary Examiner—Sabiha Qazi
(74) Attorney, Agent, or Firm—Keil & Weinkauf

(57) ABSTRACT

Fungicidal mixtures, comprising as active components
a) a compound of the formula I

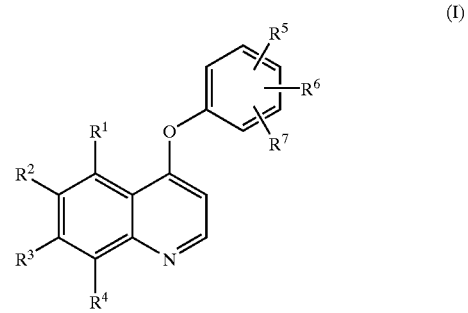

its N-oxide or one of its salts where:
$R^1$, $R^2$, $R^3$, $R^4$ independently of one another are: hydrogen, hydroxyl, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio;
$R^5$, $R^6$, $R^7$ independently of one another are: hydrogen, hydroxyl, cyano, nitro, halogen, $C_1$–$C_7$-alkyl, $C_1$–$C_7$-haloalkyl, $C_1$–$C_7$-alkoxy, $C_1$–$C_7$-haloalkoxy, $C_1$–$C_7$-alkylthio, $C_1$–$C_7$-haloalkylthio, $C_1$–$C_7$-hydroxyalkyl, $C_2$–$C_4$-acyl, aryl, aryloxy, where the radicals with aryl may for their part carry one to three of the following groups: cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio, and
b) carbamates of the formula II,

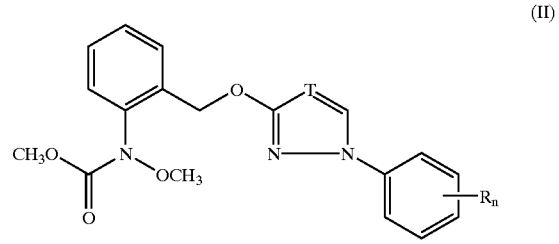

in which T is CH or N, n is 0, 1 or 2 and R is halogen, $C_1$–$C_4$-alkyl or $C_1$–$C_4$-haloalkyl, where the radicals R may be different if n is 2,
in a synergistically effective amount.

13 Claims, No Drawings

FUNGICIDE MIXTURE

This application is a 371 of PCT/EP99/09812, filed on Dec. 11, 1999 which claims priority of DE 19859250.7 filed on Dec. 22, 1998.

The present invention relates to a fungicidal mixture comprising a) a compound of the formula I

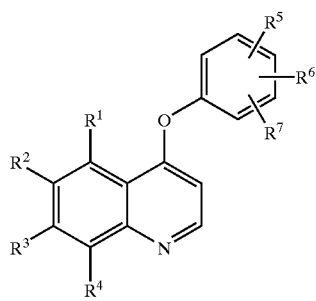

its N-oxide or one of its salts where:

$R^1$, $R^2$, $R^3$, $R^4$ independently of one another are: hydrogen, hydroxyl, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio;

$R^5$, $R^6$, $R^7$ independently of one another are: hydrogen, hydroxyl, cyano, nitro, halogen, $C_1$–$C_7$-alkyl, $C_1$–$C_7$-haloalkyl, $C_1$–$C_7$-alkoxy, $C_1$–$C_7$-haloalkoxy, $C_1$–$C_7$-alkylthio, $C_1$–$C_7$-haloalkylthio, $C_1$–$C_7$-hydroxyalkyl, $C_2$–$C_4$-acyl, aryl, aryloxy, where the radicals with aryl may for their part carry one to three of the following groups: cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio, and b) a compound of the formula II,

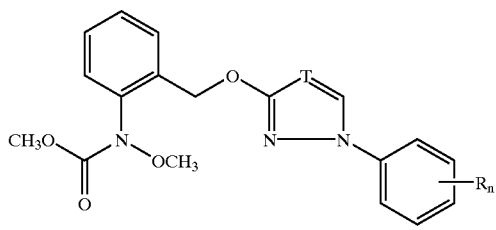

in which T is CH or N, n is 0, 1 or 2 and R is halogen, $C_1$–$C_4$-alkyl or $C_1$–$C_4$-haloalkyl, where the radicals R may be different if n is 2, in a synergistically effective amount.

Moreover, the invention relates to methods for controlling harmful fungi using the compounds I and the compounds II or synergistic mixtures comprising them, and to the use of the compounds I or the compounds II for preparing such mixtures.

Compounds of the formula I, their fungicidal action and their preparation are known from U.S. Pat. No. 5,240,940 and from ACS Sympos. Ser. 443, page 538 to page 552 (1991).

The compounds of the formula II, their preparation and their action against harmful fungi are likewise known from the literature (WO-A 96/01,256 and 96/01,258).

It is an object of the present invention to provide mixtures which, at a reduced total amount of active compounds applied, have an improved action against harmful fungi (synergistic mixtures), with a view to reducing the application rates and improving the activity spectrum of the known compounds.

We have found that this object is achieved by the mixtures defined at the outset. Furthermore, we have found that, if the compounds I and the compounds II are applied simultaneously, i.e. jointly or separately, or if the compounds I and the compounds II are applied successively, harmful fungi can be controlled better than with the compounds I or II on their own.

Owing to the basic character of the nitrogen ring atom or the NH grouping, the compounds I and II are capable of forming salts with inorganic or organic acids or with metal ions.

Examples of inorganic acids are hydrohalic acids, such as hydrogen fluoride, hydrogen chloride, hydrogen bromide and hydrogen iodide, sulfuric acid, phosphoric acid and nitric acid or carbonic acid.

Suitable organic acids are, for example: formic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of from 1 to 20 carbon atoms), arylsulfonic acids or aryldisulfonic acids (aromatic radicals, such as phenyl and naphthyl, which carry one or two sulfo groups), alkylphosphonic acids (phosphonic acids having straight-chain or branched alkyl radicals of from 1 to 20 carbon atoms), arylphosphonic acids or aryldiphosphonic acids (aromatic radicals, such as phenyl and naphthyl, which carry one or two phosphonic acid radicals), it being possible for the alkyl or aryl radicals to carry further substituents, for example p-toluene sulfonic acid, salicylic acid, p-aminosalicylic acid, 2-phenoxybenzoic acid, 2-acetoxybenzoic acid, etc.

Suitable metal ions are, in particular, the ions of the elements of the second main group, in particular calcium and magnesium, the third and fourth main group, in particular aluminum, tin and lead, and the first to eighth sub-group, in particular chromium, manganese, iron, cobalt, nickel, copper, zinc. Particular preference is given to the metal ions of the elements of the sub-groups of the fourth period. The metals can exist in the various valencies which they can assume.

Furthermore, the compounds I can be converted in a manner known per se into the N-oxides (cf. U.S. Pat. No. 5,240,940).

With respect to the C=Y or C=CH or C=N double bonds, the compounds of the formula II can be present in the E or the Z configuration (with respect to the carboxylic acid function). Accordingly, they can be used in the mixture according to the invention in each case either as pure E or Z isomers or as E/Z isomer mixtures. Preference is given to using the E/Z isomer mixture or the Z isomer, and particular preference is given to the Z isomer.

The C=N double bonds of the oxime ether groupings in the side chain of the compounds II can in each case be present as pure E or Z isomers or as E/Z isomer mixtures. The compounds II can be used in the mixtures according to the invention both as isomer mixtures and as pure isomers. With respect to their use, particular preference is given to compounds II in which the terminal oxime ether grouping of the side chain is present in the cis configuration ($OCH_3$ to $COOCH_3$).

For providing the fungicidal mixtures according to the invention, preference is given to using compounds I, their salts or N-oxides in which:

$R^1, R^2, R^3, R^4$ independently of one another are hydrogen, halogen, $C_1$–$C_2$-alkyl, $C_1$–$C_2$-haloalkyl, $C_1$–$C_2$-alkoxy, $C_1$–$C_2$-haloalkoxy or $C_1$–$C_2$-alkylthio;

$R^5, R^6, R^7$ independently of one another are hydrogen, nitro, cyano, halogen, $C_1$–$C_4$-alkyl, $C_1$–$C_4$-haloalkyl, $C_1$–$C_4$-alkoxy or phenyl.

With respect to the suitability for use as mixing partners, particular preference is given to the compounds Ia of Table 1 below.

TABLE 1

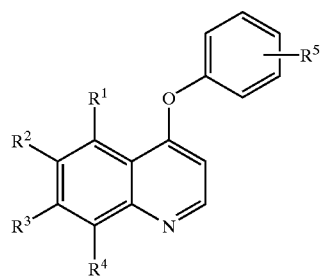

(Ia)

| No. | $R^1$ | $R^2$ | $R^3$ | $R^4$ | $R^5$ |
|---|---|---|---|---|---|
| I.1 | H | H | Cl | H | 2-F |
| I.2 | H | H | Cl | H | 2-C(CH$_3$)$_3$ |
| I.3 | H | H | Cl | H | 2-CH$_3$ |
| I.4 | H | H | Cl | H | 2-OCH$_3$ |
| I.5 | H | H | Cl | H | 3-F |
| I.6 | H | H | Cl | H | 3-Cl |
| I.7 | H | H | Cl | H | 3-CF$_3$ |
| I.8 | H | H | Cl | H | 3-CN |
| I.9 | H | H | Cl | H | 3-OCH$_3$ |
| I.10 | H | H | Cl | H | 3-phenyl |
| I.11 | H | H | Cl | H | 4-Cl |
| I.12 | H | H | Cl | H | 4-Br |
| I.13 | H | H | Cl | H | 4-CF$_3$ |
| I.14 | H | H | Cl | H | 4-CH$_3$ |
| I.15 | H | H | Cl | H | 4-CH(CH$_3$)$_2$ |
| I.16 | H | H | Cl | H | 4-CN |
| I.17 | H | H | Cl | H | 2-Cl-4-F |
| I.18 | H | H | Cl | H | 2,4-di-Br |
| I.19 | H | H | Cl | H | 2,4-di-NO$_2$ |
| I.20 | H | H | Cl | H | 2-CH$_3$-4-F |
| I.21 | H | H | Cl | H | 2,6-di-F |
| I.22 | H | H | Cl | H | 2,4,6-tri-CH$_3$ |
| I.23 | F | H | H | H | 4-F |
| I.24 | Cl | H | H | H | 4-F |
| I.25 | NO$_2$ | H | H | H | 4-F |
| I.26 | H | F | H | H | 4-F |
| I.27 | H | Cl | H | H | 4-F |
| I.28 | H | CH$_3$ | H | H | 4-F |
| I.29 | H | NO$_2$ | H | H | 4-F |
| I.30 | H | OC$_2$H$_5$ | H | H | 4-F |
| I.31 | H | H | F | H | 4-F |
| I.32 | H | H | Cl | H | 4-F |
| I.33 | H | H | Br | H | 4-F |
| I.34 | H | H | NO$_2$ | H | 4-F |
| I.35 | H | H | OCF$_3$ | H | 4-F |
| I.36 | H | H | C$_2$H$_5$ | H | 4-F |
| I.37 | H | H | SCF$_3$ | H | 4-F |
| I.38 | H | H | O—C$_2$H$_5$ | H | 4-F |
| I.39 | H | H | H | F | 4-F |
| I.40 | H | H | H | Cl | 4-F |
| I.41 | H | H | H | CF$_3$ | 4-F |
| I.42 | F | H | F | H | 4-F |
| I.43 | O—CH$_3$ | H | O—CH$_3$ | H | 4-F |
| I.44 | Cl | F | H | H | 4-F |
| I.45 | Cl | Cl | H | H | 4-F |
| I.46 | Cl | CH$_3$ | H | H | 4-F |
| I.47 | H | Br | H | Cl | 4-F |
| I.48 | H | Cl | H | OH | 4-F |
| I.49 | H | O—CH$_3$ | H | NO$_2$ | 4-F |
| I.50 | H | F | Cl | H | 4-F |

TABLE 1-continued (Ia)

| No. | $R^1$ | $R^2$ | $R^3$ | $R^4$ | $R^5$ |
|---|---|---|---|---|---|
| I.51 | H | CH$_3$ | Cl | H | 4-F |
| I.52 | H | H | Cl | Cl | 4-F |
| I.53 | Cl | H | H | Cl | 4-F |
| I.54 | Cl | F | Cl | H | 4-F |
| I.55 | H | H | Cl | CN | 4-F |
| I.56 | Cl | CH$_3$ | Cl | H | 4-F |
| I.57 | Cl | Cl | Cl | H | 4-F |
| I.58 | Cl | Cl | Cl | Cl | 4-F |
| I.59 | H | H | H | Cl | 2-F-4-Br |
| I.60 | H | H | H | Cl | 2,3-di-CH$_3$ |
| I.61 | H | H | H | Cl | 2-F-4-Cl |
| I.62 | H | H | H | Cl | 2,4-di-Cl-6-F |
| I.63 | H | H | H | Cl | 2,4-di-F |
| I.64 | H | H | H | Cl | 2,4-di-CH$_3$ |
| I.65 | H | H | H | Cl | 2-C$_2$H$_5$ |
| I.66 | H | H | H | Cl | 2-CH$_3$-4-F |
| I.67 | H | H | H | Cl | 3-CH$_3$-4-Cl |
| I.68 | H | H | Cl | H | H |
| I.69 | Cl | H | Cl | H | H |
| I.70 | H | H | Cl | H | 4-C(CH$_3$)$_3$ |

Very particular preference is given to the compounds Ia of Table 2 and to the hydrochloride and the N-oxide of the compound 8 mentioned therein.

TABLE 2

| No. | $R^1$ | $R^2$ | $R^3$ | $R^4$ | $R^5$ |
|---|---|---|---|---|---|
| 1.71 | H | H | Cl | H | 2-Cl |
| 1.72 | H | H | Cl | H | 2-Br |
| 1.73 | H | H | Cl | H | 2-CN |
| 1.74 | H | H | Cl | H | 2-CF$_3$ |
| 1.75 | H | H | Cl | H | 2-NO$_2$ |
| 1.76 | H | H | Cl | H | 4-F |
| 1.77 | H | H | Cl | H | 2,4-di-F |
| 1.78 | Cl | H | Cl | H | 4-F |
| 1.79 | H | H | H | Cl | 2-Cl-4-F |
| 1.80 | CH$_3$ | H | CH$_3$ | H | 4-F |

The compounds of the formula Ia mentioned in or under Tables 1 and 2 are known from U.S. Pat. No. 5,240,940 and/or ACS Sympos. Ser. 443, page 538 to page 552 (1991). Compound I.78 of Table 2 is known under the common name quinoxyfen.

For providing the fungicidal mixtures according to the invention, preference is given to compounds II in which T and R are as defined in Table 3.

TABLE 3

| No. | T | $R_n$ |
|---|---|---|
| II.1 | N | 2-F |
| II.2 | N | 3-F |
| II.3 | N | 4-F |

TABLE 3-continued

| No. | T | R$_n$ |
|---|---|---|
| II.4 | N | 2-Cl |
| II.5 | N | 3-Cl |
| II.6 | N | 4-Cl |
| II.7 | N | 2-Br |
| II.8 | N | 3-Br |
| II.9 | N | 4-Br |
| II.10 | N | 2-CH$_3$ |
| II.11 | N | 3-CH$_3$ |
| II.12 | N | 4-CH$_3$ |
| II.13 | N | 2-CH$_2$CH$_3$ |
| II.14 | N | 3-CH$_2$CH$_3$ |
| II.15 | N | 4-CH$_2$CH$_3$ |
| II.16 | N | 2-CH(CH$_3$)$_2$ |
| II.17 | N | 3-CH(CH$_3$)$_2$ |
| II.18 | N | 4-CH(CH$_3$)$_2$ |
| II.19 | N | 2-CF$_3$ |
| II.20 | N | 3-CF$_3$ |
| II.21 | N | 4-CF$_3$ |
| II.22 | N | 2,4-F$_2$ |
| II.23 | N | 2,4-Cl$_2$ |
| II.24 | N | 3,4-Cl$_2$ |
| II.25 | N | 2-Cl 4-CH$_3$ |
| II.26 | N | 3-Cl 4-CH$_3$ |
| II.27 | CH | 2-F |
| II.28 | CH | 3-F |
| II.29 | CH | 4-F |
| II.30 | CH | 2-Cl |
| II.31 | CH | 3-Cl |
| II.32 | CH | 4-Cl |
| II.33 | CH | 2-Br |
| II.34 | CH | 3-Br |
| II.35 | CH | 4-Br |
| II.36 | CH | 2-CH$_3$ |
| II.37 | CH | 3-CH$_3$ |
| II.38 | CH | 4-CH$_3$ |
| II.39 | CH | 2-CH$_2$CH$_3$ |
| II.40 | CH | 3-CH$_2$CH$_3$ |
| II.41 | CH | 4-CH$_2$CH$_3$ |
| II.42 | CH | 2-CH(CH$_3$)$_2$ |
| II.43 | CH | 3-CH(CH$_3$)$_2$ |
| II.44 | CH | 4-CH(CH$_3$)$_2$ |
| II.45 | CH | 2-CF$_3$ |
| II.46 | CH | 3-CF$_3$ |
| II.47 | CH | 4-CF$_3$ |
| II.48 | CH | 2,4-F$_2$ |
| II.49 | CH | 2,4-Cl$_2$ |
| II.50 | CH | 3,4-Cl$_2$ |
| II.51 | CH | 2-Cl 4-CH$_3$ |
| II.52 | CH | 3-Cl 4-CH$_3$ |

Particular preference is given to the compounds II.12, II.23, II.32 and II.38.

In some cases, it has been found to be advantageous to use other fungicidally active compounds in addition to the fungicidally active compounds I and II in the mixtures according to the invention. Mention may be made in particular of active compounds from the group of the azoles or the morpholine and piperidine derivatives.

Particularly preferred azoles are the compounds mentioned below:

bromuconazole, Proc. Br. Crop Prot. Conf.-Pests Dis., 5-6, 439 (1990);

cyproconazole, U.S. Pat. No. 4,664,696;

difenoconazole, GB-A 2,098,607;

diniconazole, CAS RN [83657-24-3];

epoxiconazole, EP-A 196 038;

fenbuconazole (proposed), EP-A 251 775;

fluquinconazole, Proc. Br. Crop Prot. Conf.-Pests Dis., 5-3, 411 (1992);

flusilazole, Proc. Br. Crop Prot. Conf.-Pests Dis., 1, 413 (1984);

hexaconazole, CAS RN [79983-71-4];

metconazole, Proc. Br. Crop Prot. Conf.-Pests Dis., 5-4, 419 (1992);

prochloraz, U.S. Pat. No. 3,991,071;

propiconazole, GB-A 1,522,657;

tebuconazole, U.S. Pat. No. 4,723,984;

tetraconazole, Proc. Br. Crop Prot. Conf.-Pests Dis., 1, 49 (1988);

triflumizole, JP-A 79/119,462 flutriafol, CAS RN [76674-21-0]

myclobutanil, CAS RN [88671-89-0].

A particularly preferred mixing partner is epoxiconazole.

In such ternary mixtures, the ratios of the triazoles to the compounds I and II are generally in the range of from 20:1 to 1:20, preferably from 10:1 to 1:10.

Suitable morpholine or piperidine derivatives are, in particular, the known active compounds tridemorph, fenpropidin and fenpropimorph, which are commercially available. Particular preference is given here to fenpropimorph. The ratios of the morpholine or piperidine derivatives to the compounds I and II are generally in the range of from 50:1 to 1:10, preferably from 25:1 to 1:1.

Finally, in some other cases it has been found to be advantageous to use quaternary mixtures which, in addition to compounds I and II, comprise a triazole and a morpholine or piperidine derivative. A mixture which is preferred in practice is a mixture of compounds I (in particular compound I.78 from Table 2), compounds II (preferably compounds II.32 or II.38 from Table 3), epoxiconazole and fenpropimorph.

When preparing the mixtures, it is preferred to employ the pure active compounds I and II, to which further active compounds against harmful fungi or other pests, such as insects, arachnids or nematodes, or else herbicidal or growth-regulating active compounds or fertilizers can be admixed, as required.

The mixtures of the compounds I and II, or the compounds I and II, applied simultaneously, i.e. jointly or separately, or successively, exhibit outstanding activity against a wide range of phytopathogenic fungi, in particular from the classes of the Ascomycetes, Deuteromycetes, Phycomycetes and Basidiomycetes. Some of them act systemically and can therefore be employed as foliar- and soil-acting fungicides.

They are especially important for controlling a large number of fungi in a variety of crop plants, such as cotton, vegetable species (for example cucumbers, beans and cucurbits), barley, grass, oats, coffee, maize, fruit species, rice, rye, soya, grapevine, wheat, ornamentals, sugarcane, and a variety of seeds.

They are particularly suitable for controlling the following phytopathogenic fungi: *Erysiphe graminis* (powdery mildew) in cereals, *Erysiphe cichoracearum* and *Sphaerotheca fuliginea* in cucurbits, *Podosphaera leucotricha* in apples, Puccinia species in cereals, Rhizoctonia species in cotton and lawns, Ustilago species in cereals and sugarcane, *Venturia inaequalis* (scab) in apples, Helminthosporium species in cereals, *Septoria nodorum* in wheat, *Botrytis cinerea* (gray mold) in strawberries and grapes, *Cercospora arachidicola* in groundnuts, Pseudocercosporella herpotrichoides in wheat and barley, *Pyricularia oryzae* in rice, Phytophthora infestans in potatoes and tomatoes, *Plasmopara viticola* in grapes, Alternaria species in vegetables and fruit, and also Fusarium and Verticillium species.

Furthermore, they can be used in the protection of materials (for example in the protection of wood), for example against *Paecilomyces variotii*.

The compounds I and II can be applied simultaneously, i.e. together or separately, or in succession, the sequence, in the case of separate application, generally not having any effect on the result of the control measures.

The compounds I and II are usually used in a weight ratio of from 50:1 to 0.1:1, preferably from 25:1 to 0.5:1, in particular from 10:1 to 1:1.

Depending on the kind of effect desired, the application rates of the mixtures according to the invention are from 0.01 to 3 kg/ha, preferably from 0.1 to 1.5 kg/ha, in particular from 0.4 to 1.0 kg/ha.

The application rates of the compounds I are from 0.01 to 0.5 kg/ha, preferably from 0.05 to 0.5 kg/ha, in particular from 0.05 to 0.2 kg/ha.

Depending on the kind of effect desired, the application rates of the mixtures according to the invention for the compounds II are from 0.005 to 0.5 kg/ha, preferably from 0.05 to 0.5 kg/ha, in particular from 0.05 to 0.2 kg/ha.

For seed treatment, the application rates of the mixture are generally from 0.001 to 50 g/kg of seed, preferably from 0.01 to 10 g/kg, in particular from 0.01 to 8 g/kg.

If phytopathogenic fungi are to be controlled, the separate or joint application of the compounds I and II or of the mixtures of the compounds I and II is effected by spraying or dusting the seeds, the plants or the soils before or after sowing of the plants, or before or after plant emergence.

The fungicidal synergistic mixtures according to the invention, or the compounds I and II, can be formulated, for example, in the form of directly sprayable solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should ensure as fine and uniform as possible a distribution of the mixture according to the invention.

The formulations are prepared in a manner known per se, for example by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, for example ligno-, phenol-, naphthalene- and dibutylnaphthalene-sulfonic acid, and of fatty acids, alkyl- and alkylaryl-sulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methyl cellulose.

Powders, materials for broadcasting and dusts can be prepared by mixing or jointly grinding the compounds I and II, or the mixtures of the compounds I and II with a solid carrier.

Granules (for example coated granules, impregnated granules or homogeneous granules) are usually prepared by binding the active compound, or active compounds, to a solid carrier.

Fillers or solid carriers are, for example, mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise from 0.1 to 95% by weight, preferably from 0.5 to 90% by weight, of one of the compounds I and II. The active compounds are employed in a purity of from 90% to 100%, preferably from 95% to 100% (according to NMR spectrum or HPLC).

The compounds I and II, or the mixtures, or the corresponding formulations, are applied by treating the harmful fungi or the plants, seeds, soils, areas, materials or spaces to be kept free from them with a fungicidally effective amount of the mixture, or of the compounds I and II in the case of separate application. Application can be effected before or after infection by the harmful fungi.

The fungicidal activity of the compounds and the mixtures can be demonstrated by the following experiments:

The active compounds, separately or together, are formulated as a 10% strength emulsion in a mixture of 70% by weight of cyclohexanone, 20% by weight of Nekanil® LN (Lutensol® AP6, wetting agent having emulsifying and dispersing action based on ethoxylated alkylphenols) and 10% by weight of Emulphor® EL (Emulan® EL, emulsifier based on ethoxylated fatty alcohols) and diluted with water to the desired concentration.

Evaluation is carried out by determining the infected leaf areas in percent. These percentages are converted into efficacies. The expected efficacies of the mixtures of the active compounds are determined using Colby's formula [R. S. Colby, Weeds 15, 20–22 (1967)] and compared with the observed efficacies.

Colby's formula:

$$E = x + y + z - x \cdot y \cdot z / 100$$

E expected efficacy, expressed in % of the untreated control, when using the mixture of the active compounds A, B and C at the concentrations a, b and c x efficacy, expressed in % of the untreated control, when using active compound A at a concentration of a y efficacy, expressed in % of the untreated control, when using active compound B at a concentration of b z efficacy, expressed in % of the untreated control, when using active compound C at a concentration of c The efficacy (E) is calculated as follows using Abbot's formula:

$$E = (1 - \alpha/\beta) \cdot 100$$

α corresponds to the fungal infection of the treated plants in % and

β corresponds to the fungal infection of the untreated (control) plants in %

At an efficacy of 0, the infection level of the treated plants corresponds to that of the untreated control plants; at an efficacy of 100, the treated plants are not infected.

USE EXAMPLE 1

Action Against Mildew of Wheat

Leaves of wheat seedlings of the cultivar "Kanzler", grown in pots, were sprayed to run-off point with an aqueous formulation of active ingredient which had been prepared using a stock solution comprising 10% of active ingredient, 63% of cyclohexanone and 27% of emulsifier, and 24 h after the spraycoating had dried on the leaves were dusted with spores of mildew of wheat (*Erysiphe graminis* forma specialis tritici). The test plants were subsequently placed in climatized chambers at 20–24° C. and 60–90% relative atmospheric humidity for 7 days. The extent of the development of the disease on the leaves was then evaluated visually.

The visually determined values for the percentage of diseased leaf area were converted into efficacies in % of the untreated control. An efficacy of 0 means the same disease level as in the untreated control, an efficacy of 100 means a disease level of 0%. The expected efficacies for the active ingredient combinations were determined using Colby's formula (Colby, S. R. "Calculating synergistic and antagonistic responses of herbicide combinations", Weeds, 15, pp. 20–22, 1967) and compared with the observed efficacies.

The components II were the compounds II.23, II.32 and II.38 from Table 3.

| Ex. | Active ingredient | conc. in ppm | Efficacy in % of the untreated control |
|---|---|---|---|
| 1C | without | (90% diseased) | 0 |
| 2C | Compound I.78 | 1 | 33 |
| | (common name: | 0.25 | 0 |
| | quinoxyfen) | 0.06 | 0 |
| 3C | Compound II.23 | 4 | 78 |
| | | 1 | 67 |
| | | 0.25 | 11 |
| | | 0.06 | 0 |
| 4C | Compound II.32 | 1 | 67 |
| | | 0.25 | 11 |
| | | 0.06 | 0 |
| 5C | Compound II.38 | 4 | 78 |
| | | 1 | 67 |
| | | 0.25 | 11 |
| | | 0.06 | 0 |

TABLE 5

| Ex. | Mixture according to the invention (conc. in ppm) | Observed efficacy | Calculated efficacy* |
|---|---|---|---|
| 6 | 1 ppm I.78 + 1 ppm II.23 | 93 | 78 |
| 7 | 0.25 ppm I.78 + 0.25 ppm II.23 | 44 | 11 |
| 8 | 0.06 ppm I.78 + 0.06 ppm II.23 | 21 | 0 |
| 9 | 1 ppm I.78 + 4 ppm II.23 | 97 | 85 |
| 10 | 0.25 ppm I.78 + 1 ppm II.23 | 94 | 67 |
| 11 | 1 ppm I.78 + 0.25 ppm II.23 | 56 | 41 |
| 12 | 0.25 ppm I.78 + 0.06 ppm II.23 | 21 | 0 |
| 13 | 1 ppm I.78 + 1 ppm II.32 | 94 | 78 |
| 14 | 0.25 ppm I.78 + 0.25 ppm II.32 | 56 | 11 |
| 15 | 0.06 ppm I.78 + 0.06 ppm II.32 | 21 | 0 |
| 16 | 0.06 ppm I.78 + 0.25 ppm II.32 | 32 | 11 |
| 17 | 1 ppm I.78 + 0.25 ppm II.32 | 78 | 41 |
| 18 | 0.25 ppm I.78 + 0.06 ppm II.32 | 21 | 0 |
| 19 | 1 ppm I.78 + 1 ppm II.38 | 93 | 78 |

TABLE 5-continued

| Ex. | Mixture according to the invention (conc. in ppm) | Observed efficacy | Calculated efficacy* |
|---|---|---|---|
| 20 | 0.25 ppm I.78 + 0.25 ppm II.38 | 32 | 11 |
| 21 | 0.06 ppm I.78 + 0.06 ppm II.38 | 21 | 0 |
| 22 | 1 ppm I.78 + 4 ppm II.38 | 100 | 85 |
| 23 | 1 ppm I.78 + 0.25 ppm II.38 | 67 | 41 |
| 24 | 0.25 ppm I.78 + 0.06 ppm II.38 | 21 | 0 |

*Calculated using Colby's formula

The test results show that for all mixing ratios the observed efficacy is higher than the efficacy which had been calculated beforehand using Colby's formula.

We claim:

1. A fungicidal composition comprising, as active components, a) a compound of formula I (I)

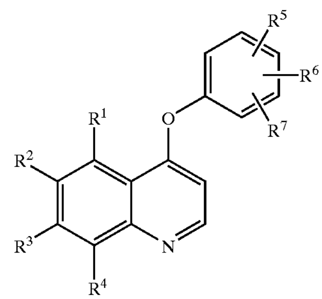

its N-oxide or one of its salts where:

$R^1$, $R^2$, $R^3$, $R^4$ independently of one another are: hydrogen, hydroxyl, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio;

$R^5$, $R^6$, $R^7$ independently of one another are: hydrogen, hydroxyl, cyano, nitro, halogen, $C_1$–$C_7$-alkyl, $C_1$–$C_7$-haloalkyl, $C_1$–$C_7$-alkoxy, $C_1$–$C_7$-haloalkoxy, $C_1$–$C_7$-alkylthio, $C_1$–$C_7$-haloalkylthio, $C_1$–$C_7$-hydroxyalkyl, $C_2$–$C_4$-acyl, aryl, aryloxy, where the radicals with aryl may for their part carry one to three of the following groups: cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio, and b) at least one carbamate of formula II, (II)

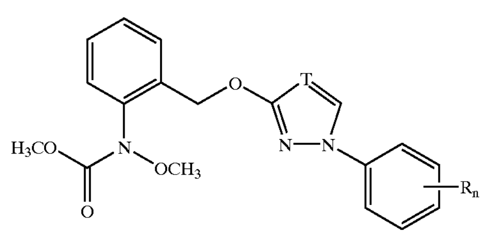

wherein T is CH or N, n is 0, 1 or 2 and R is halogen, $C_1$–$C_4$-alkyl or $C_1$–$C_4$-haloalkyl, and where the radicals R are identical or different when n is 2, wherein the active components (a) and (b) are present in synergistically effective amounts.

2. The composition defined in claim 1, wherein the components (a) and (b) are present in a weight ratio of from 20:1 to 1:20.

3. The composition defined in claim 1, which comprises as a further active component an effective amount of a fungicidal triazole.

4. The composition defined in claim 1, which comprises as a further active component an effective amount of one or more compounds selected from the group consisting of fenpropimorph, fenpropidin and tridodemorph.

5. The composition defined in claim 3, which comprises as a further active component an effective amount, of one or more compounds selected from the group consisting of fenpropimorph, fenpropidin and tridemorph.

6. A method for controlling harmful fungi, which comprises treating the harmful fungi, their habitat or plants, seeds, soils, areas, materials or spaces to be kept from said fungi with an effective amount of the composition defined in claim 1.

7. The method of claim 6, wherein the active components (a) and (b) are applied simultaneously either jointly or separately, or successively.

8. The method of in claim 6, wherein the the active component (a) is applied in an amount of from 0.01 to 0.5 kg/ha.

9. A process for preparing the composition defined in claim 1, which comprises admixing synergistically effective amounts of the active components (a) and (b).

10. The composition defined in claim 1 which is conditioned in two parts, one part comprising the component (a) in a solid or liquid carrier and the other part comprising the component (b) in a a solid or liquid carrier.

11. The composition defined in claim 3, wherein the fungicidal triazole is selected from the group consisting of bromuconazole, cyproconazole, difenoconazole, diniconazole, epoxiconazole, fenbuconazole, fluquinconazole, flusilazole, hexaconazole, metconazole, prochloraz, propiconazole, tebuconazole, tetraconazole, triflumizole, flutriafol and myclobutanil.

12. The composition defined in claim 3, wherein the further active component and the components (a) and (b) are present in a weight ratio of from 20:1 to 1:20.

13. The composition defined in claim 4, wherein the further active component and the components (a) and (b) are present in a weight ratio of from 50:1 to 1:10.

* * * * *